(12) United States Patent
Kikuchi

(10) Patent No.: US 11,625,635 B2
(45) Date of Patent: Apr. 11, 2023

(54) COMPUTER-READABLE STORAGE MEDIUM STORING CONTROL PROGRAM, CONTROL METHOD, AND CONTROL DEVICE

(71) Applicant: FUJITSU LIMITED, Kawasaki (JP)

(72) Inventor: Ryota Kikuchi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 1016 days.

(21) Appl. No.: 16/398,695

(22) Filed: Apr. 30, 2019

(65) Prior Publication Data

US 2019/0347564 A1 Nov. 14, 2019

(30) Foreign Application Priority Data

May 14, 2018 (JP) .............................. JP2018-093374

(51) Int. Cl.
| | | |
|---|---|---|
| G06N 7/01 | (2023.01) | |
| C12Q 1/06 | (2006.01) | |
| G06F 16/11 | (2019.01) | |
| G06N 3/00 | (2023.01) | |
| C12M 1/34 | (2006.01) | |
| C12Q 3/00 | (2006.01) | |

(52) U.S. Cl.
CPC ................. G06N 7/01 (2023.01); C12M 1/34 (2013.01); C12Q 1/06 (2013.01); C12Q 3/00 (2013.01); G06F 16/116 (2019.01); G06N 3/00 (2013.01)

(58) Field of Classification Search
CPC .......... G06N 7/005; G06N 3/00; G06N 20/20; C12M 1/34; C12Q 1/06; C12Q 3/00; G06F 16/116
See application file for complete search history.

(56) References Cited

U.S. PATENT DOCUMENTS

| | | | | |
|---|---|---|---|---|
| 2005/0130255 A1* | 6/2005 | Montijn | ................. | C12Q 1/025 435/34 |
| 2006/0246444 A1* | 11/2006 | van der Vossen | ..... | C12Q 1/025 435/6.1 |

(Continued)

FOREIGN PATENT DOCUMENTS

| | | |
|---|---|---|
| JP | 2004-164237 | 6/2004 |
| JP | 2006-509506 | 3/2006 |
| JP | 2007-061064 | 3/2007 |

*Primary Examiner* — Santiago Garcia

(74) *Attorney, Agent, or Firm* — Fujitsu Patent Center

(57) ABSTRACT

A non-transitory computer-readable storage medium storing a control program for causing a computer to execute for acquiring, from a sensor, multiple monitored values in multistep processes including a process related to fermentation of microbes; setting probability distributions for multiple specific parameters related to unmonitored data and included in multiple parameters included in a nonlinear mathematical model related to the fermentation of the microbes corresponding to the multistep processes; generating monitoring predicted values at next monitoring time of the mathematical model based on the multiple monitored values and the probability distributions; using a distribution of the monitoring predicted values and values monitored at the next monitoring time to update the multiple parameters; and controlling the mathematical model so that errors of the multiple specific parameters generated using the mathematical model including the updated multiple parameters are reduced.

10 Claims, 10 Drawing Sheets

(56) References Cited

U.S. PATENT DOCUMENTS

| | | | |
|---|---|---|---|
| 2008/0288528 A1* | 11/2008 | Gallager | G01N 33/1866 707/999.102 |
| 2010/0248320 A1* | 9/2010 | Lyons | A23K 10/38 435/165 |
| 2012/0004111 A1* | 1/2012 | Colwell | G16B 50/30 506/8 |
| 2013/0265191 A1* | 10/2013 | Ghinamo | G01S 19/42 342/357.23 |
| 2016/0224721 A1* | 8/2016 | Neymann | G16B 5/30 |
| 2017/0247652 A1* | 8/2017 | Goluch | C12M 1/34 |
| 2018/0237815 A1* | 8/2018 | Ichikawa | C12N 1/14 |

\* cited by examiner

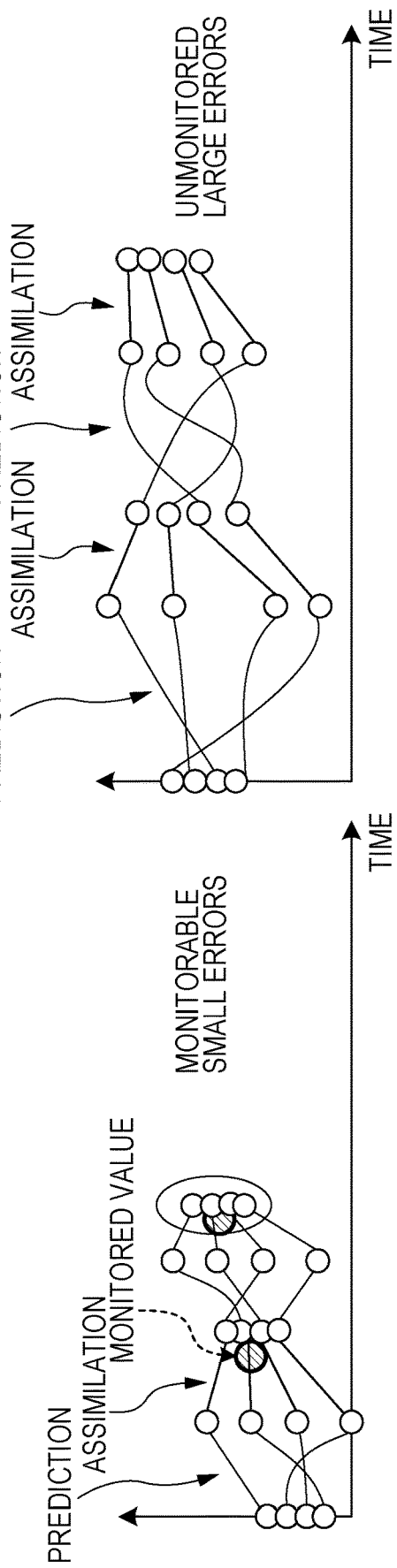

COMPUTER-READABLE STORAGE MEDIUM STORING CONTROL PROGRAM, CONTROL METHOD, AND CONTROL DEVICE

CROSS-REFERENCE TO RELATED APPLICATION

This application is based upon and claims the benefit of priority of the prior Japanese Patent Application No. 2018-93374, filed on May 14, 2018, the entire contents of which are incorporated herein by reference.

FIELD

The embodiments discussed herein are related to a computer-readable storage medium storing a control program, a control method, and a control device.

BACKGROUND

In a production process using fermentation of microbes, such as the brewing of Japanese sake, multistep activities of the microbes are used. In a process of producing Japanese sake, when temperature management or a brewing plan is erroneously conducted, the quality or yield of Japanese sake may be reduced. Thus, in the process of producing Japanese sake, a brewing plan for a next day is created based on monitored data such as a temperature during brewing, an alcohol content, a Baumé degree, a Japanese sake degree, and an amino acid content to improve the yield.

Examples of related art are Japanese Laid-open Patent Publication No. 2007-061064, Japanese Laid-open Patent Publication No. 2004-164237, and Japanese National Publication of International Patent Application No. 2006-509506.

SUMMARY

According to an aspect of the embodiments, a non-transitory computer-readable storage medium storing a control program for causing a computer to execute for acquiring, from a sensor, multiple monitored values in multistep processes including a process related to fermentation of microbes; setting probability distributions for multiple specific parameters related to unmonitored data and included in multiple parameters included in a nonlinear mathematical model related to the fermentation of the microbes corresponding to the multistep processes; generating monitoring predicted values at next monitoring time of the mathematical model based on the multiple monitored values and the probability distributions; using a distribution of the monitoring predicted values and values monitored at the next monitoring time to update the multiple parameters; and controlling the mathematical model so that errors of the multiple specific parameters generated using the mathematical model including the updated multiple parameters are reduced.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 4A and 4B are diagrams describing data assimilation by an ensemble Kalman filter;

DESCRIPTION OF EMBODIMENTS

For example, as data acquired in a process of producing Japanese sake, there are a temperature in a sake barrel, an alcohol content, a Baumé degree, and the like. Activities of microbes such as *Aspergillus oryzae* and yeast are indirectly reflected in the data and significantly affect the quality of the Japanese sake. It is, however, difficult to directly monitor the microbes. Thus, even when monitorable data acquired from the sake barrel is used to predict the production process using fermentation of microbes, the accuracy of the prediction may not be high.

It is considered to convert the production process to a mathematical model using variables indicating microbial activities that are not directly monitorable. It is, however, not easy to search for a hyperparameter in the mathematical model. When parameters that indicate a temperature and an alcohol content and in which microbial activities are indirectly reflected are optimized, and the amount of data is small, overfitting may occur. Even when the temperature and the alcohol content are close to target values, microbial activities related to the temperature and the alcohol content may not be close to target activities.

Figure 10B:
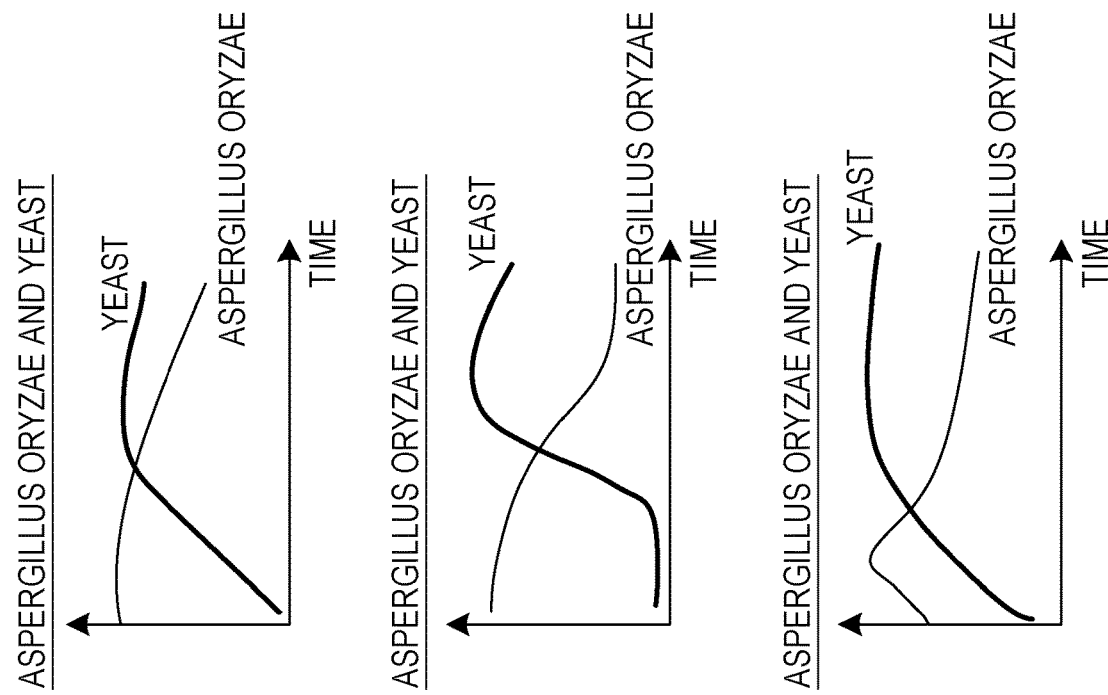
FIGS. 10A and 10B are diagrams describing overfitting.
Figure 10A:
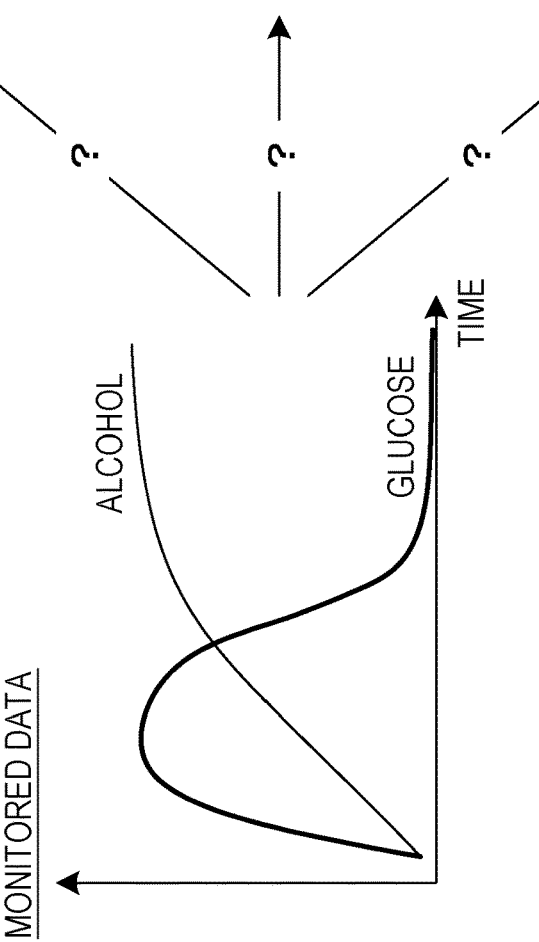

FIGS. 10A and 10B are diagrams describing the overfitting. As illustrated in FIG. 10A, since an alcohol content and the amount of glucose are monitored from the inside of a sake barrel, changes in the alcohol content and the amount of glucose over time may be acquired. *Aspergillus oryzae* and yeast are not directly monitored. Thus, as illustrated in FIG. 10B, activity amounts of microbes such as *Aspergillus oryzae* and yeast and changes in activities over time are not uniquely identified from monitored data of the alcohol content and the amount of glucose. Thus, even when a mathematical model including an unmonitorable variable is prepared and parameters are tuned in advance, it is difficult to improve the accuracy of predicting the production process.

Hereinafter, embodiments of a sequential control program disclosed herein, a sequential control method disclosed herein, and a sequential control device disclosed herein are described in detail with reference to accompanying drawings. The present disclosure is not limited by the embodiments. The embodiments may be combined without contradiction.

First Embodiment

Description of Sequential Control Device

Figure 1:
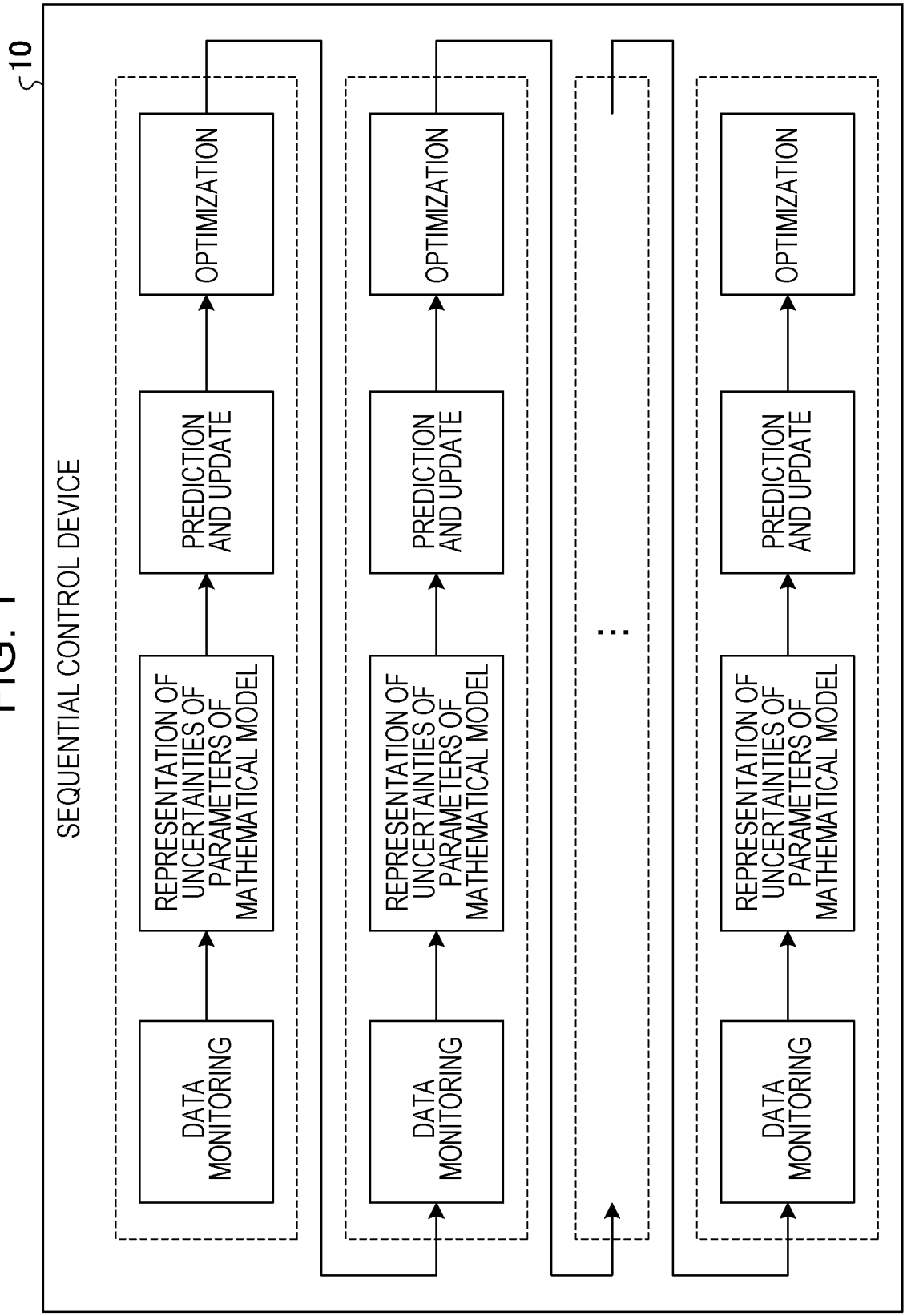
FIG. 1 is a diagram describing a sequential control device according to a first embodiment.

FIG. 1 is a diagram describing a sequential control device according to a first embodiment. The sequential control device 10 illustrated in FIG. 1 is an example of a computer device that converts a process (brewing process) of producing Japanese sake to a mathematical model and calculates time evolution of variables (parameters) included in the mathematical model to predict the production process. For example, the sequential control device 10 uses currently monitored data to execute prediction for a temperature change plan and an operation plan for another device in the brewing of Japanese sake, uses results of the prediction to calculate an optimal plan, and gives information that improves the yield.

As illustrated in FIG. 1, the sequential control device 10 generates the mathematical model for the production process. The mathematical model includes monitorable parameters that are to be monitored in a brewing container and are the amount of glucose, an alcohol content, a temperature, and the like. The mathematical model further includes unmonitored parameters that are not monitored in the brewing container and are the amount of starch, the amount of *Aspergillus oryzae,* the amount of yeast, and the like. After the generation of the mathematical model, the sequential control device 10 sequentially repeats a series of processes of monitoring data in the brewing container, representing uncertainties of the parameters included in the mathematical model, executing data prediction and parameter update, and optimizing a production plan and controls the production plan in a stepwise manner so as to cause the production plan to be close to a target plan based on results of daily manual work in the production of Japanese sake.

For example, the sequential control device 10 acquires, from a sensor, multiple monitored values in multistep processes including a process related to fermentation of microbes. The sensor may monitor multiple values among the amount of glucose, an alcohol content, a temperature, a Baumé degree, a Japanese sake degree, and an amino acid content. The sequential control device 10 sets probability distributions for multiple specific parameters related to unmonitored data and included in multiple parameters included in a nonlinear mathematical model related to the microbial fermentation and corresponding to the multistep processes. After that, the sequential control device 10 generates monitoring predicted values at next monitoring time of the mathematical model based on the multiple monitored values and the probability distributions. Then, the sequential control device 10 uses a distribution of the monitoring predicted values and the values monitored at the next monitoring time to update the multiple parameters. After that, the sequential control device 10 controls the mathematical model so that errors of the multiple specific parameters generated using the mathematical model including the updated multiple parameters are reduced.

For example, the sequential control device 10 generates multiple mathematical models (ensembles) for monitorable parameters included in the mathematical model for the production process so that allowable error ranges of the monitorable parameters included in the mathematical model for the production process are small. Then, the sequential control device 10 uses monitoring values predicted using the ensembles and actually monitored values to update the parameters.

The sequential control device 10 generates multiple ensembles so that allowable error ranges of the unmonitored parameters included in the mathematical model for the production process are large. Then, the sequential control device 10 updates the parameters using relationships with actually monitored values of the other monitorable parameters.

For example, the sequential control device 10 may learn unmonitored parameters by sequentially repeating prediction and optimization so that errors of allowable values are small. As a result, the sequential control device 10 may improve the accuracy of predicting the production process including the multistep processes related to the fermentation of the microbes, since sequential control is executed to optimize predicted parameters generated using a mathematical model related to unmonitored parameters for the production process including the multistep processes.

Functional Configuration of Sequential Control Device

Figure 2:
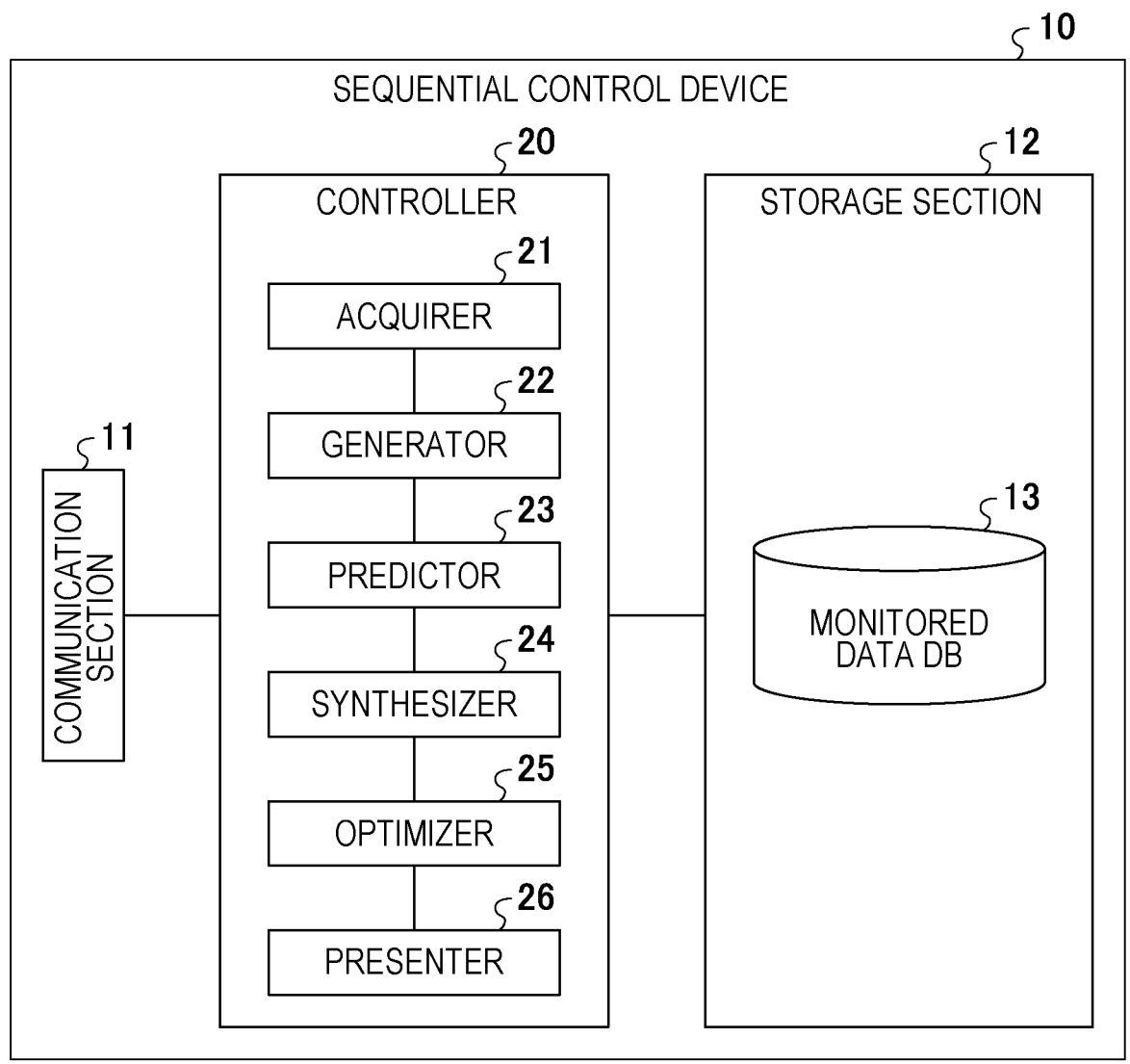
FIG. 2 is a functional block diagram illustrating a functional configuration of the sequential control device according to the first embodiment.

FIG. 2 is a functional block diagram illustrating a functional configuration of the sequential control device 10 according to the first embodiment. As illustrated in FIG. 2, the sequential control device 10 includes a communication section 11, a storage section 12, and a controller 20.

The communication section 11 is a processing section for controlling communication with another device and is, for example, a communication interface. For example, the communication section 11 receives an instruction to start a process from a terminal of an administrator. The communication section 11 transmits the results of the sequential control to the terminal of the administrator or the like.

The storage section 12 is an example of a storage device for storing a program and data and is, for example, a memory, a hard disk, or the like. The storage section 12 stores a monitored data DB 13. The monitored data DB 13 is a database for storing values monitored in a sake barrel that is an example of a brewing container. For example, the monitored data DB 13 stores monitoring time and monitorable values including the amount of glucose, an alcohol content, and a temperature so that the values are associated with the monitoring time.

The controller 20 is a processing section for controlling processes of the entire sequential control device 10 and is, for example, a processor. The controller 20 includes an acquirer 21, a generator 22, a predictor 23, a synthesizer 24, an optimizer 25, and a presenter 26. The acquirer 21, the generator 22, the predictor 23, the synthesizer 24, the optimizer 25, and the presenter 26 are an example of processes to be executed by the processor, an electronic circuit included in the processor, or the like. The processor may include one or more of a field-programmable gate array (FPGA), an application-specific integrated circuit (ASIC), a single central processing unit (CPU), a multiple CPU, and a multi-core CPU.

The acquirer 21 is a processing section for acquiring values monitored by a sensor from Japanese sake being brewed in the sake barrel to be monitored. For example, the acquirer 21 sequentially acquires monitored values to improve the accuracy while removing an uncertainty of a mathematical model described later. For example, the acquirer 21 acquires values such as the amount of glucose, an alcohol content, and a temperature periodically or at time intervals of 12 hours, one day, or the like, associates the acquired monitored values with monitoring time and days, and causes the acquired monitored values and the monitoring time and days to be stored in the monitored data DB 13. As a method for the monitoring, one or more of various known methods may be used.

The generator 22 is a processing section for generating the mathematical model for the process of producing Japanese sake and setting probability distributions representing uncertainties for parameters included in the mathematical model. For example, the generator 22 generates a nonlinear mathematical model including Equations (1) to (6) as a mathematical model including monitorable parameters and non-monitorable parameters that are an example of specific parameters. The non-monitorable parameters include not only unmonitorable parameters but also parameters to be hardly monitored and parameters that may be monitored but are hardly monitored at practical time. In this specification, a "non-monitorable parameter" may be replaced with an "unmonitored parameter".

$$dS/dt = -aSM : \text{starch} \quad (1)$$

$$dM/dt = b(T)*SM - c(T)*M : \textit{Aspergillus oryzae} \quad (2)$$

$$dG/dt = vSM - wGF : \text{glucose} \quad (3)$$

$$dF/dt = x(T)*GF - y(T)*F : \text{yeast} \quad (4)$$

$$dA/dt = zGF : \text{alcohol} \quad (5)$$

$$dT/dt = t_1 SM + t_2 GF - t_3 (T - T_{room}) : \text{a temperature} \quad (6)$$

Equation (1) is a non-monitorable parameter and is a mathematical model indicating a change in the amount of starch over time and defining that the starch is broken down when the starch and *Aspergillus oryzae* exist. Equation (2) is a non-monitorable parameter and is a mathematical model indicating a change in the amount of *Aspergillus oryzae* over time and defining that the starch is broken down and grows so that a certain amount of *Aspergillus oryzae* becomes extinct. Equation (3) is a monitorable parameter and is a mathematical model indicating a change in the amount of glucose over time and defining that the *Aspergillus oryzae* generates glucose and sake yeast is broken down and reduced in amount.

Equation (4) is a non-monitorable parameter and is a mathematical model indicating a change in the amount of yeast over time and defining that the glucose is broken down and grows so that a certain amount of glucose becomes extinct. Equation (5) is a monitorable parameter and is a mathematical model indicating a change in an alcohol content over time and defining that sake yeast is generated. Equation (6) is a monitorable parameter and is a mathematical model indicating a change in a temperature in the sake barrel over time and defining that heat is generated due to activities of fungus and thermal exchange with the outside of the sake barrel occurs according to Newton's law of cooling.

In Equations (1) to (6), S indicates the amount of the starch, M indicates the amount of the *Aspergillus oryzae*, G indicates the amount of the glucose, F is the amount of the yeast, A indicates the alcohol content, T indicates the temperature in the sake barrel, and $T_{room}$ indicates a temperature of a room in which the sake barrel is placed. In Equations (1) to (6), a is a coefficient related to a reduced amount of the starch, b is a coefficient related to an increased amount of the *Aspergillus oryzae*, c(T) is a function of a temperature related to a reduced amount of the *Aspergillus oryzae*, v is a coefficient related to an increased amount of the glucose, w is a coefficient related to a reduced amount of the glucose, x(T) is a function of a temperature related to the increased amount of the *Aspergillus oryzae*, y(T) is a function of a temperature related to a reduced amount of the yeast, z is a coefficient related to an increased amount of the alcohol, $t_1$ is a coefficient related to heat generated by the *Aspergillus oryzae*, $t_2$ is a coefficient related to heat generated by the yeast, and $t_3$ is a coefficient related to thermal exchange with the temperature of the room.

The generator 22 causes the mathematical model to have a margin using a probability distribution in order to represent an uncertainty included in the mathematical model and a monitoring error (measurement error) included in the mathematical model. Thus, the generator 22 quantifies a certainty of a predicted value of the mathematical model using an unmonitored physical amount and a monitored physical amount. After initial setting, the spread of ensembles is directly used. For example, the generator 22 sets a probability distribution including values predicted by the predictor 23 for the ensembles.

For example, the generator 22 generates a probability distribution for which a high uncertainty is set for each of an unmonitored physical amount and a physical amount with a large monitoring error among the parameters defined in the aforementioned equations. For example, the generator 22 generates a probability distribution for which a low uncertainty is set for a physical amount with a small monitoring error among the parameters defined in the aforementioned equations. For example, the generator 22 sets a standard deviation of a Gaussian distribution for a parameter with a high uncertainty to be large and sets a standard deviation of a Gaussian distribution for a parameter with a low uncertainty to be small. Then, the generator 22 generates multiple mathematical models (ensembles) based on the set probability distributions.

Figures 3A, 3B:
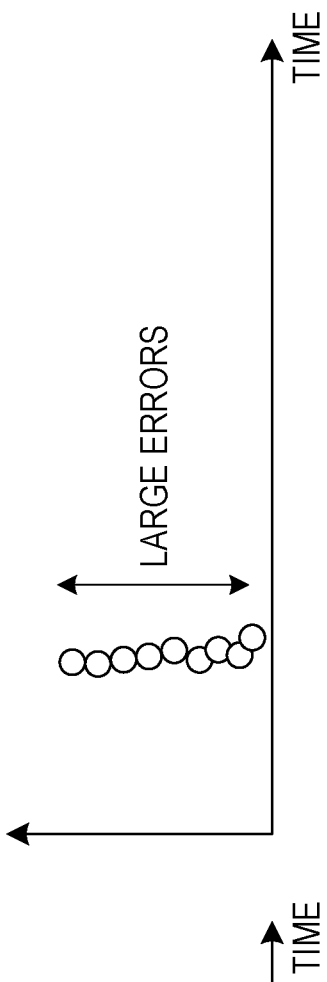
FIGS. 3A and 3B are diagrams describing the generation of ensembles representing uncertainties.

FIGS. 3A and 3B are diagrams describing the generation of ensembles representing uncertainties. FIG. 3A is a diagram describing the generation of ensembles for a temperature that is a monitorable parameter and includes a small monitoring error. As illustrated in FIG. 3A, since a parameter such as the temperature has a low uncertainty, multiple ensembles with small errors with respect to a monitored value are generated. FIG. 3B is a diagram describing the generation of ensembles for a non-monitorable parameter. As illustrated in FIG. 3B, a parameter such as yeast has a high uncertainty, multiple ensembles with large errors are generated.

For example, the generator 22 uses the method described with reference to FIG. 3A to generate multiple ensembles for the monitorable parameters indicated by Equations (3), (5), and (6). In addition, the generator 22 uses the method described with reference to FIG. 3B to generate multiple ensembles for the non-monitorable parameters indicated by Equations (1), (2), and (4).

The predictor 23 is a processing section for generating monitoring predicted values at next monitoring time of the mathematical model generated by the generator 22 based on the multiple monitored values acquired by the acquirer 21 and the probability distributions set by the generator 22. For example, the predictor 23 calculates predicted values of parameters using a mathematical model representing an uncertainty.

For example, the predictor 23 prepares and calculates multiple mathematical models (ensembles) including parameters different for probability distributions, thereby recognizing, from the spread of the probability distributions, how uncertainties indicated by unmonitored physical amounts affect the calculation of the mathematical models.

For example, the predictor 23 uses Equation (6) to calculate monitoring predicted values at the next monitoring time. The predictor 23 uses Equation (6) to calculate predicted values for ensembles generated for the temperature. In this manner, the predictor 23 sequentially executes a process of calculating the monitoring predicted values at the next monitoring time for ensembles, generated by the generator 22, of the parameters.

The synthesizer 24 is a processing section for updating the parameters of the mathematical model using distributions of the monitoring predicted values and values actually monitored at the next monitoring time. For example, the synthesizer 24 updates the parameters of the mathematical model using monitored values and prediction results of the mathematical model when the monitored values are acquired. For example, the synthesizer 24 updates the parameters by synthesizing the actually monitored values with ensembles (data assimilation) to estimate the unmonitored parameters with high accuracy.

For example, the synthesizer 24 uses ensembles representing uncertainties and an ensemble Kalman filter to approximate probability distributions between multiple models for the ensembles and execute data assimilation. The ensemble Kalman filter is one of methods for assimilating sequential data. FIGS. 4A and 4B are diagrams describing the data assimilation by the ensemble Kalman filter. As illustrated in FIG. 4A, when a monitored value exists (in the case of a monitorable parameter), state estimation (Bayesian update) is executed on the monitored value. As illustrated in FIG. 4B, when a monitored value does not exist (in the case of a non-monitorable parameter), a correlation relationship between the parameter and another parameter is identified from a covariance matrix of ensembles, and the state estimation is executed using the correlation relationship.

Figure 5:
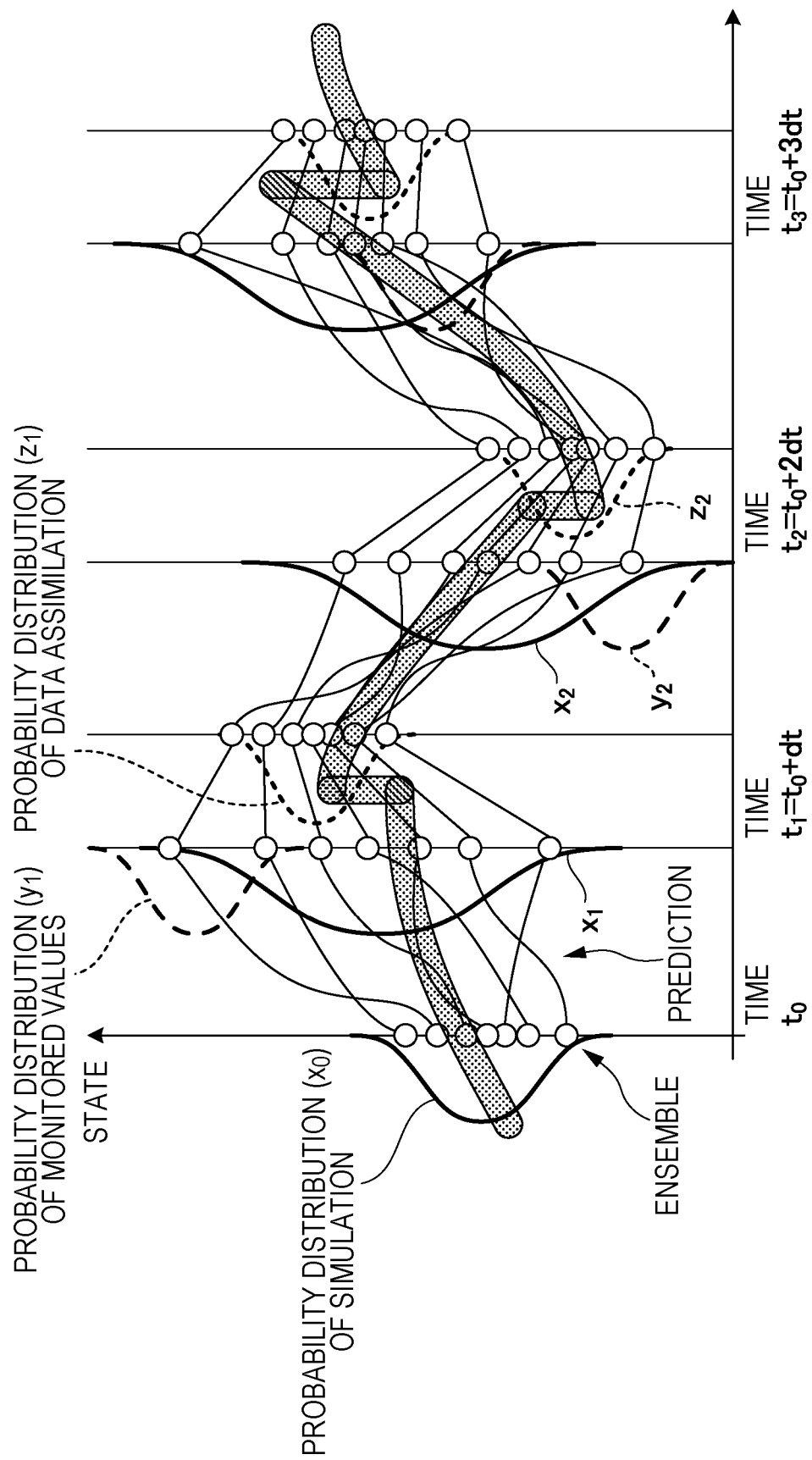
FIG. 5 is a diagram describing parameter update by data assimilation.

The flow of sequential data assimilation is described using a parameter "temperature" as an example. FIG. 5 is a diagram describing parameter update by the data assimilation. As illustrated in FIG. 5, at time $t_0$, the generator 22 sets a probability distribution $x_0$ with a low set uncertainty and generates multiple ensembles based on the set probability distribution $x_0$.

Subsequently, at time $t_1$, the predictor 23 calculates predicted values from the ensembles generated at the time $t_0$, and the acquirer 21 acquires a monitored value of the temperature. Then, the synthesizer 24 generates a probability distribution $y_1$ based on an error of the monitored value of the temperature and a probability distribution $x_1$ of the predicted values calculated from the ensembles and generates a probability distribution $z_1$, obtained by synthesizing the probability distributions with each other, of data assimilation. After that, the generator 22 generates multiple ensembles based on the probability distribution $z_1$ and updates the parameter "temperature".

Subsequently, at time $t_2$, the predictor 23 calculates predicted values from the ensembles generated at the time $t_1$, and the acquirer 21 acquires a monitored value of the temperature. Then, the synthesizer 24 generates a probability distribution $y_2$ based on an error of the monitored value of the temperature and a probability distribution $x_2$ of the predicted values calculated from the ensembles and generates a probability distribution $z_2$, obtained by synthesizing the probability distributions with each other, of data assimilation. After that, the generator 22 generates multiple ensembles based on the probability distribution $z_2$ and updates the parameter "temperature".

When only simple prediction is executed, an error increases and a probability distribution spreads out over time. The sequential control device 10, however, may sequentially update a parameter while correcting predicted values using a probability distribution of monitored values. A monitorable physical amount (parameter) is updated based on a monitored value and a predicted value. An unmonitorable physical amount (parameter) is estimated from a monitored value of another parameter and updated. This process is executed on each of parameters of a mathematical model. As a result, an unmonitored physical amount may be estimated with high accuracy from the synthesis of an acquired monitored value with a mathematical model by using the ensemble Kalman filter for a physical amount (*Aspergillus oryzae* or the like) to be monitored during a long time period normally and a physical amount unmonitorable in principle.

Returning to FIG. 2, the optimizer 25 is a processing section for controlling a mathematical model so that errors of multiple specific parameters generated using the mathematical model including an updated parameter are reduced. For example, the optimizer 25 executes optimization control based on an objective function using results of predicting ensembles of a mathematical model updated by the synthesizer 24.

An unmonitored physical amount may be updated using a monitored value. A mathematical model, however, includes an uncertainty. Even when the optimization control is executed on each of ensembles, the optimization control leads to different solutions. The optimizer 25 treats all ensembles as a single group and executes model prediction control on a parameter to be controlled so that an objective function for all the ensembles is improved.

Figure 6A:
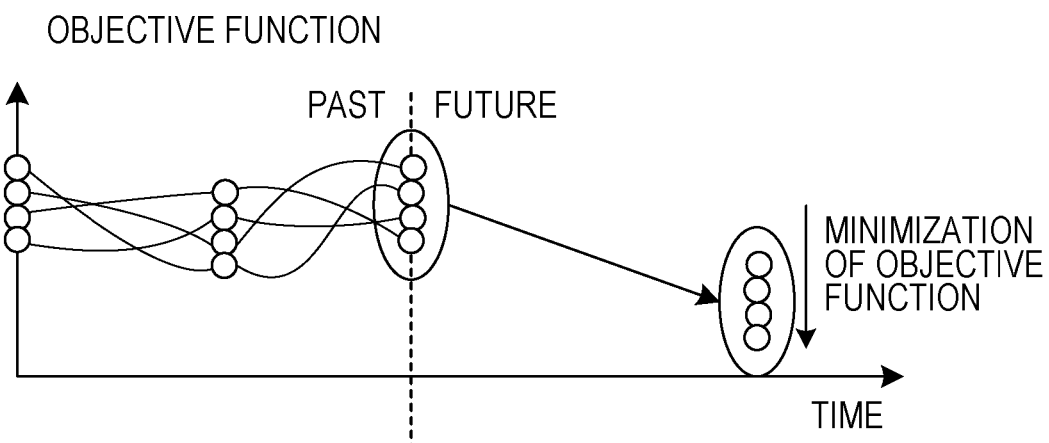
FIGS. 6A and 6B are diagrams describing the minimization of an objective function.
Figure 6B:
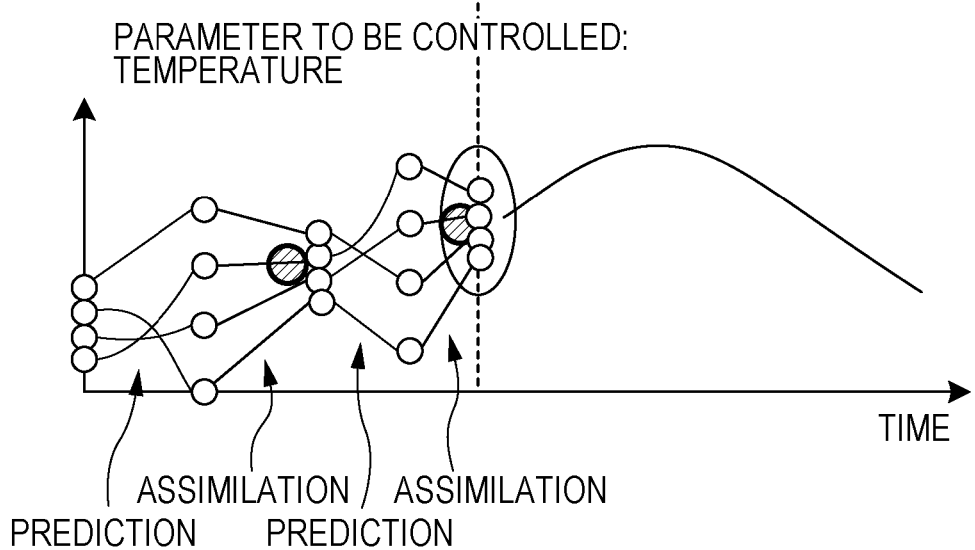

FIGS. 6A and 6B are diagrams describing the minimization of the objective function. As illustrated in FIG. 6A, as the model prediction control, the optimizer 25 generates a distribution of the parameter to be controlled, executes prediction using a mathematical model, calculates the objective function, and minimizes the objective function. For example, as illustrated in FIG. 6B, when the parameter to be controlled is the temperature, the generator 22 generates multiple ensembles, the predictor 23 calculates predicted values at next monitoring time for the ensembles, and the synthesizer 24 executes data assimilation on the ensembles using an actually measured value (monitored value) and the predicted values and generates multiple ensembles with the updated parameter. After that, the optimizer 25 estimates the quality of Japanese sake using a known equation (law) for calculating the quality of Japanese sake from the temperature and controls all the multiple ensembles so that a difference between the quality and a target quality is reduced.

Figure 7:
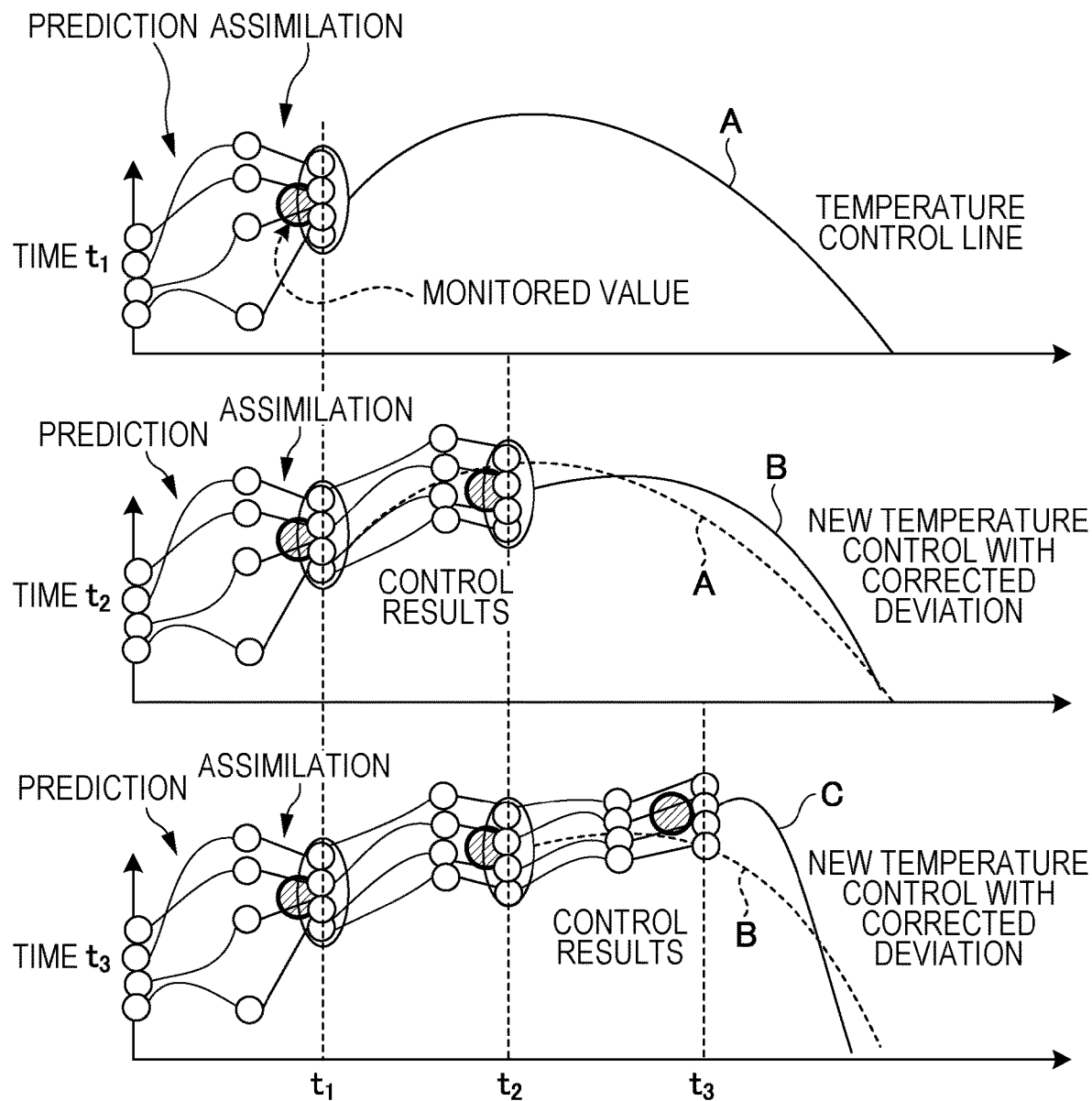
FIG. 7 is a diagram describing optimization control.

The sequential control for the optimization is described using temperature control as an example. FIG. 7 is a diagram describing the optimization control. As illustrated in FIG. 7, at time $t_1$, the optimizer 25 calculates a temperature control line A for all ensembles identified by data assimilation at the time $t_1$. After that, at time $t_2$, the optimizer 25 calculates a temperature control line B for all ensembles identified by data assimilation at the time $t_2$ in order to correct an error caused by manual temperature control performed after the time $t_1$, and executes new temperature control to correct a deviation of the temperature control line B from the temperature control line A calculated at the time $t_1$.

At time $t_3$, the optimizer 25 calculates a temperature control line C for all ensembles identified by data assimilation at the time $t_3$ in order to correct an error caused by manual temperature control after the time $t_2$, and executes new temperature control to correct a deviation of the temperature control line C from the temperature control line B calculated at the time $t_2$. In this manner, the optimizer 25 sequentially repeats temperature control to cause the temperature to reach a target temperature while correcting a difference between the temperature control predicted at each of the time points and a manual operation performed for the temperature control.

The presenter 26 is a processing section for presenting results of the optimization control by the optimizer 25 to a user. For example, the presenter 26 transmits, to a user terminal, a message indicating that the temperature in the sake barrel is to be changed to a temperature (of, for example, 20° C.) identified by the optimizer 25. For example, the presenter 26 displays the message on a display unit such as a display included in the sequential control device 10. The presenter 26 may display the temperature control lines illustrated in FIG. 7 to the user.

Flow of Process

Figure 8:
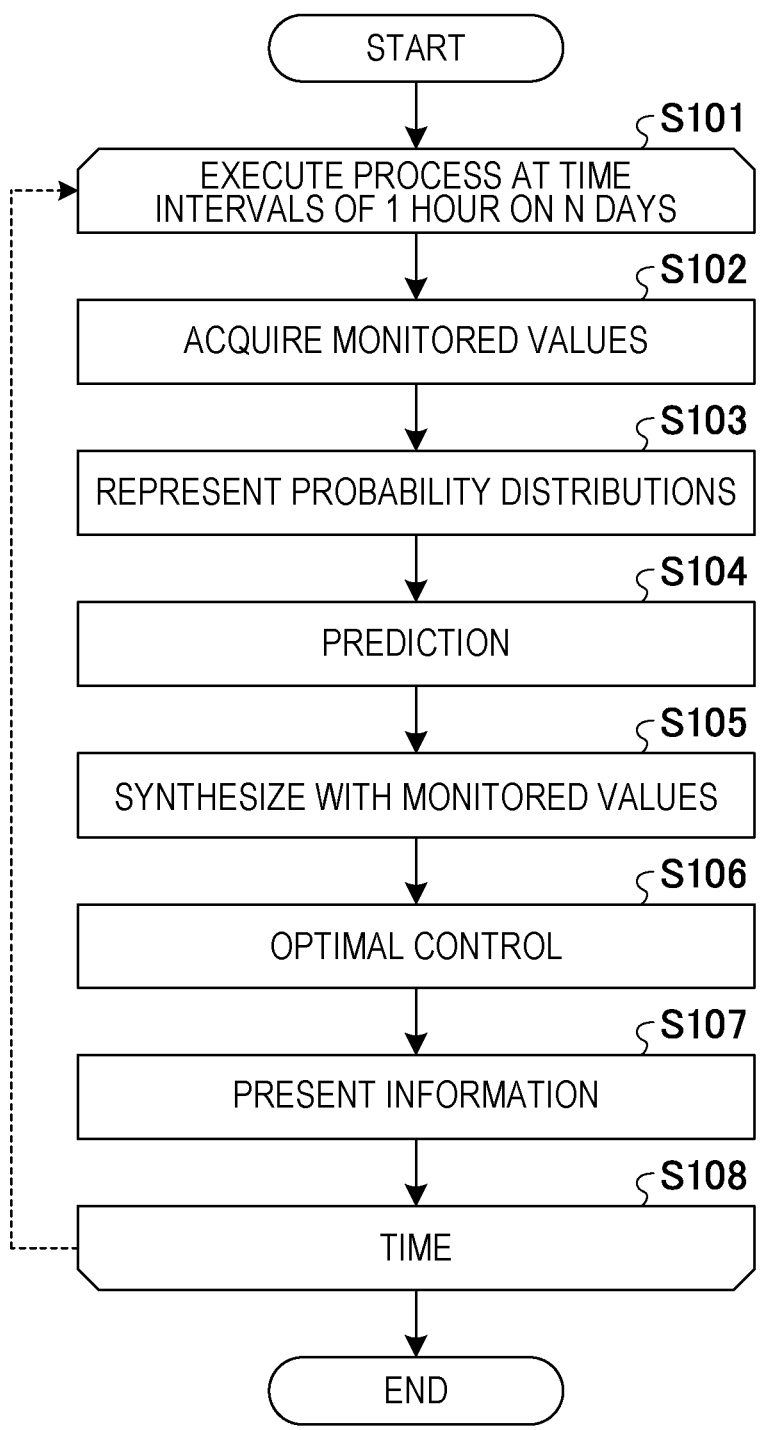
FIG. 8 is a flowchart illustrating the flow of a process.

FIG. 8 is a flowchart illustrating the flow of a process. As illustrated in FIG. 8, the sequential control device 10 sequentially executes processes of S101 to S108 at time intervals of, for example, one hour on N (N is a natural number) days.

For example, the acquirer 21 monitors multiple values and acquires the multiple monitored values in the process of producing Japanese sake (in S102). Sequentially, the generator 22 builds a mathematical model for the production process and sets probability distributions representing uncertainties for parameters included in the mathematical model (in S103).

Then, the predictor 23 executes prediction and calculation using the mathematical model representing uncertainties with ensembles (in S104). Sequentially, the synthesizer 24 assimilates (synthesizes) the monitored values with results of executing the prediction using the mathematical model to update the parameters of the mathematical model when the monitored values are acquired (in S105).

After that, the optimizer 25 uses results of predicting ensembles of the updated mathematical model to execute the optimization control based on an objective function (in S106). Then, the presenter 26 presents information such as results of the optimization control (in S107). Wait the time until the next execution starts at the time interval of 1 hour (in S108).

Effects

As described above, the sequential control device 10 may enable the sequential control of optimizing predicted parameters generated using a mathematical model related to unmonitored data for the production process including the multistep processes related to the fermentation of the microbes. As a result, the sequential control device 10 may improve the accuracy of predicting the production process.

Usually, in prediction using a mathematical model, when an error or loss of an unmonitored physical amount or monitored value exists, it is difficult to appropriately execute the prediction. For example, in the process of producing Japanese sake, since a monitored value may include a large error or a large loss, depending on a portion monitored in a sake barrel, and a value is manually monitored, it is difficult to appropriately acquire all values monitored during a brewing time period. In addition, on a day on which values are monitored, a plan for the next day is to be determined. Thus, physical amounts that are the amount of yeast, the amount of *Aspergillus oryzae,* and the like and are to be monitored during long time periods are not used. A Baumé degree (Japanese sake degree) and the like are monitored by dipping Japanese sake from a sake barrel. Monitored values of the Baumé degree and the like vary a depth and location of a Japanese sake barrel. Thus, an objective function for control may not be included in a general mathematical model and it is difficult to execute prediction.

On the other hand, the sequential control device 10 according to the first embodiment sequentially repeats a series of processes of monitoring data in a sake barrel, representing uncertainties of parameters of a mathematical model, executing data prediction and parameter update, and optimizing a production plan, thereby controlling the minimization of the objective function at each monitoring time point while predicting a non-monitorable parameter and correcting an monitoring error of a monitorable parameter.

As a result, temperature management that is important for the brewing of Japanese sake may be appropriately executed and a difference between a production plan and manual work may be corrected. Thus, appropriate prediction may be executed using a mathematical model, and a reduction in the quality of Japanese sake and degradation in the yield may be reduced.

Second Embodiment

Although the first embodiment is described above, the disclosure may be enabled in different embodiments other than the first embodiment.

Targets

Although the first embodiment describes the process of brewing Japanese sake, the first embodiment is not limited to this. Brewed beverages such as wine, beer, cider may be processed in the same manner. Although the first embodiment describes the temperature control as an example, the first embodiment is not limited to this. Another parameter such as an alcohol content may be processed in the same manner.

Parameters

The parameters described in the first embodiment are examples. Parameters are not limited to the parameters described in the first embodiment. A nonlinear mathematical model including another parameter to be used for the production of Japanese sake may be generated. The first embodiment describes, as an example of the synthesis of the probability distributions, the data assimilation using the ensemble Kalman filter. Another known method may be used for the synthesis of the probability distributions.

System

The process procedure, the control procedure, the specific names, the information including the various types of data and the parameters that are described in this specification with reference to the accompanying drawings may be arbitrarily changed unless otherwise specified. The specific examples, the distributions, the values, and the like that are described in the first embodiment are examples and may be arbitrarily changed.

The constituent elements of the devices illustrated in the drawings are functionally conceptual and may not be physically configured as illustrated in the drawings. Specific forms of distribution and integration of the devices are not limited to those illustrated in the drawings. For example, all or some of the devices may be distributed or integrated functionally or physically in arbitrary units based on various loads, usage states, and the like. All or some of the processing functions to be executed in the devices may be enabled by a CPU and a program analyzed and executed by the CPU or may be enabled by hardware by wired logic.

Hardware

Figure 9:
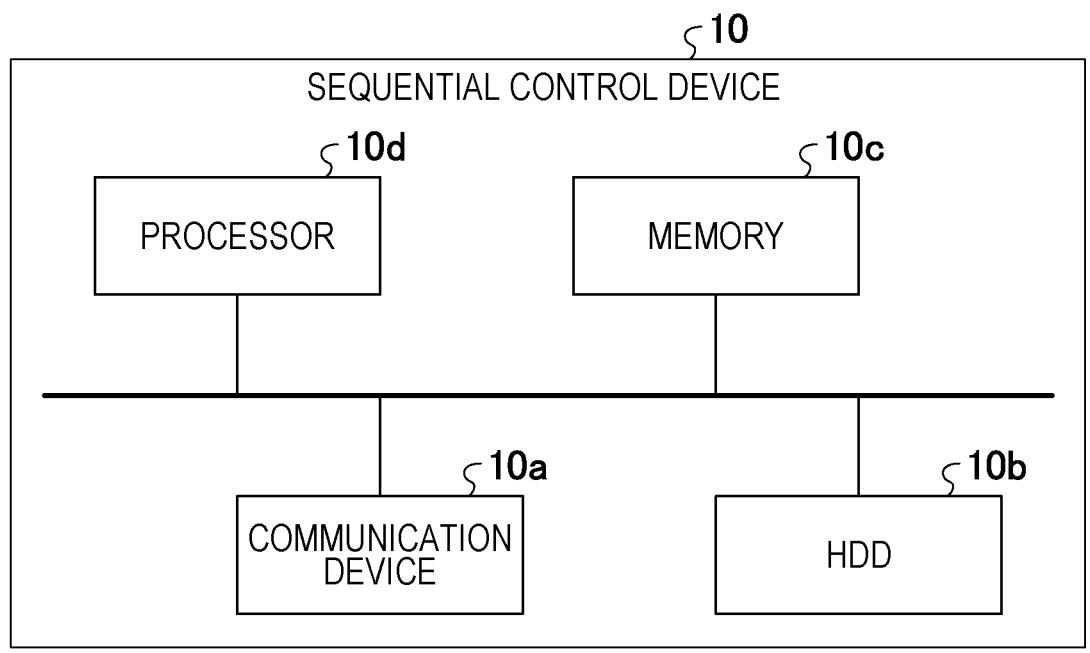
FIG. 9 is a diagram describing an example of a hardware configuration.

FIG. 9 is a diagram describing an example of a hardware configuration. As illustrated in FIG. 9, the sequential control device 10 includes a communication device 10*a*, a hard disk drive (HDD) 10*b*, a memory 10*c*, and a processor 10*d*. The units 10*a*, 10*b*, 10*c*, and 10*d* illustrated in FIG. 9 are connected to each other via a bus or the like.

The communication device 10*a* is a network interface card or the like and communicates with another server. The HDD 10*b* stores a DB and a program for executing the functions described with reference to FIG. 2.

The processor 10*d* reads, from the HDD 10*b* or the like, the program for executing the same processes as those to be executed by the processing sections illustrated in FIG. 2, loads the read program into the memory 10c, and executes a process of executing the functions described with reference to FIG. 2 and the like. The process executes the same functions as those of the processing sections included in the sequential control device 10. For example, the processor 10d reads, from the HDD 10b or the like, the program having the same functions as those of the acquirer 21, the generator 22, the predictor 23, the synthesizer 24, the optimizer 25, the presenter 26, and the like. Then, the processor 10d executes a process of executing the same processes to be executed by the acquirer 21, the generator 22, the predictor 23, the synthesizer 24, the optimizer 25, the presenter 26, and the like.

The sequential control device 10 operates as an information processing device configured to execute the sequential control method by reading and executing the program. The sequential control device 10 may cause a medium reading device to read the program from a storage medium, executes the read program, and enables the same functions as described in the first embodiment. The program according to a second embodiment may not be executed by the sequential control device 10. For example, the disclosure is applicable to the case where another computer or another server executes the program or the case where the other computer and the other server collaborate with each other to execute the program.

The program may be distributed via a network such as the Internet. The program may be stored in a computer-readable storage medium such as a hard disk, a flexible disk (FD), a CD-ROM, a magneto-optical (MO) disk, or a digital versatile disc (DVD), read by a computer from the storage medium, and executed by the computer.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable storage medium storing a control program for causing a computer to execute a process, the process comprising:
    acquiring, from a sensor, multiple monitored values in multistep processes including a process related to fermentation of microbes;
    setting probability distributions for multiple specific parameters related to unmonitored data and included in multiple parameters included in a nonlinear mathematical model related to the fermentation of the microbes corresponding to the multistep processes;
    generating monitoring predicted values at next monitoring time of the mathematical model based on the multiple monitored values and the probability distributions;
    updating the multiple parameters using a distribution of the monitoring predicted values and values monitored at the next monitoring time; and
    controlling the mathematical model so that errors of the multiple specific parameters generated using the mathematical model including the updated multiple parameters are reduced,
    wherein the updating uses an ensemble Kalman filter to generate a distribution of values obtained by assimilating the distribution of the monitoring predicted values and a distribution in which errors of the values monitored at the next monitoring time are allowable, and updates the multiple parameters in accordance with the distribution of the values obtained by the assimilation.

2. The non-transitory computer-readable storage medium according to claim 1,
    wherein the acquiring monitors the amount of glucose, an alcohol content, a temperature from a brewing container containing Japanese sake during brewing in a process of producing the Japanese sake, and
    wherein the mathematical model includes monitorable parameters that are the amount of the glucose, the alcohol content, and the temperature and non-monitorable parameters that are the amount of starch, the amount of Aspergillus Oryza, and the amount of yeast.

3. The non-transitory computer-readable storage medium according to claim 2,
    wherein the setting generates probability distributions for the monitorable parameters so that uncertainties of the probability distributions for the monitorable parameters are lower than uncertainties of probability distributions generated for the non-monitorable parameters, and
    wherein the generating generates multiple mathematical models based on the probability distributions representing the uncertainties for the monitorable parameters and the non-monitorable parameters and uses the multiple mathematical models to generate multiple monitoring predicted values corresponding to the multiple mathematical models.

4. The non-transitory computer-readable storage medium according to claim 3,
    wherein the updating generates, for each of the monitorable parameters, a distribution of values obtained by assimilating a distribution of multiple monitoring predicted values and a distribution in which errors of monitored values are allowable and updates parameters of the multiple mathematical models in accordance with the distributions of the values obtained by the assimilation.

5. The non-transitory computer-readable storage medium according to claim 3,
    wherein the updating uses, for each of the non-monitorable parameters, the ensemble Kalman filter to assimilate a distribution of multiple monitoring predicted values and values estimated from correlation relationships identified from a covariance matrix between the other monitorable parameters to generate a distribution of the assimilated values, and updates parameters of the multiple mathematical models in accordance with the distributions of the assimilated values.

6. The non-transitory computer-readable storage medium according to claim 1,
    wherein the mathematical model includes one or more of a model indicating a change over time in the amount of the microbes, a model indicating a change over time in the amount of a substance broken down and reduced in amount by the microbes, a model indicating a change over time in the amount of a substance generated and increased in amount by the microbes, and a model indicating a change over time in a temperature due to the fermentation.

7. A control method executed by a computer, comprising:

acquiring, from a sensor, multiple monitored values in multistep processes including a process related to fermentation of microbes;

setting probability distributions for multiple specific parameters related to unmonitored data and included in multiple parameters included in a nonlinear mathematical model related to the fermentation of the microbes corresponding to the multistep processes;

generating monitoring predicted values at next monitoring time of the mathematical model based on the multiple monitored values and the probability distributions;

using a distribution of the monitoring predicted values and values monitored at the next monitoring time to update the multiple parameters; and controlling the mathematical model so that errors of the multiple specific parameters generated using the mathematical model including the updated multiple parameters are reduced, wherein the updating uses an ensemble Kalman filter to generate a distribution of values obtained by assimilating the distribution of the monitoring predicted values and a distribution in which errors of the values monitored at the next monitoring time are allowable, and updates the multiple parameters in accordance with the distribution of the values obtained by the assimilation.

8. A control device comprising:

a processor configured to:

acquire, from a sensor, multiple monitored values in multistep processes including a process related to fermentation of microbes;

set probability distributions for multiple specific parameters related to unmonitored data and included in multiple parameters included in a nonlinear mathematical model related to the fermentation of the microbes corresponding to the multistep processes;

generate monitoring predicted values at next monitoring time of the mathematical model based on the multiple monitored values and the probability distributions;

use a distribution of the monitoring predicted values and values monitored at the next monitoring time to update the multiple parameters; and control the mathematical model so that errors of the multiple specific parameters generated using the mathematical model including the updated multiple parameters are reduced, wherein the use of the distribution includes using an ensemble Kalman filter to generate a distribution of values obtained by assimilating the distribution of the monitoring predicted values and a distribution in which errors of the values monitored at the next monitoring time are allowable, and updates the multiple parameters in accordance with the distribution of the values obtained by the assimilation.

9. The non-transitory computer-readable storage medium according to claim 1, wherein the process further comprises:

changing, based on the multiple specific parameters generated using the mathematical model, at least one parameter during an execution of the multistep processes.

10. The non-transitory computer-readable storage medium according to claim 9, wherein the at least one parameter is a temperature.

* * * * *